United States Patent [19]

Offermanns et al.

[11] 4,144,340

[45] Mar. 13, 1979

[54] BASIC SUBSTITUTED XANTHINE DERIVATIVES

[75] Inventors: Heribert Offermanns, Hanau; Karl H. Klingler, Langen; Klaus Thiemer, Hanau; Fritz Stroman, Offenbach, all of Fed. Rep. of Germany

[73] Assignee: Deutsche Gold und Silber-Scheideanstalt vormals Roessler, Frankfurt, Fed. Rep. of Germany

[21] Appl. No.: 786,936

[22] Filed: Apr. 12, 1977

[30] Foreign Application Priority Data

Apr. 15, 1976 [GB] United Kingdom .............. 1554/76

[51] Int. Cl.$^2$ .................. A61K 31/52; C07D 473/08; C07D 473/10
[52] U.S. Cl. ........................... 424/253; 544/273
[58] Field of Search ............ 260/256; 424/253; 544/273

[56] References Cited

U.S. PATENT DOCUMENTS

| | | | |
|---|---|---|---|
| 3,855,221 | 12/1974 | Klingler | 260/256 |
| 3,984,413 | 10/1976 | Metz et al. | 260/256 |

*Primary Examiner*—Donald G. Daus
*Assistant Examiner*—D. B. Springer
*Attorney, Agent, or Firm*—Cushman, Darby & Cushman

[57] ABSTRACT

There are prepared compounds corresponding to the general formula

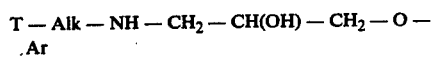

in which T represents a theophyllinyl-(7) or theobrominyl-(1) radical, Alk is a linear or branched alkylene group with 2 to 5 carbon atoms which may also be substituted by a hydroxy group and Ar represents an aromatic monocyclic or condensed bicyclic, carbocyclic or heterocyclic radical optionally substituted by one or more alkyl groups with 1 to 6 carbon atoms, alkenyl groups with 2 to 6 carbon atoms, alkinyl groups with 2 to 6 carbon atoms, hydroxy groups, acyloxy groups with 1 to 6 carbon atoms, alkoxy groups with 1 to 6 carbon atoms, alkenoxy groups with 2 to 6 carbon atoms, phenyl radicals, halogen atoms, amino groups, acyl groups with 2 to 6 carbon atoms, aminocarbonyl groups, ureido groups, acyl amino groups with 1 to 6 carbon atoms, cycloalkyl groups with 3 to 8 carbon atoms or by one or more cycloalkenyl groups with 4 to 8 carbon atoms, the heterocyclic radical consisting of individual rings with 5 to 6 members and containing from 1 to 4 heteroatoms, and their pharmaceutically acceptable salts. The compounds have beta-adrenolytic activity.

27 Claims, No Drawings

BASIC SUBSTITUTED XANTHINE DERIVATIVES

This invention relates to basically substituted xanthine derivatives.

It is known that for example compounds corresponding to the following formula

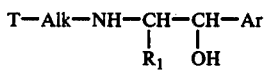

in which T represents a theophyllinyl-(7) radical $R_1$ represents a hydrogen atom or a methyl group, Ar represents a phenyl radical optionally substituted by one or more hydroxy groups, methyl groups or hydroxy methyl groups and Alk can represent a linear or branched lower alkylene group or, where Ar is an o-dihydroxy phenyl radical, may also represent the group —$CH_2$—$CH(OH)$—$CH_2$—, have a broncholytic effect (cf. German Patent Specification No. 1,545,725, German Patent Specification No. 1,545,749 and German Offenlegungsschrifts 2,136,643 (and related Klinger U.S. Pat. No. 3,728,346); 2,243,735 (and related Klinger U.S. Pat. No. 3,855,221) and 2,253,073 (and related Klinger U.S. Pat. No. 3,896,119).

The present invention relates to new xanthine derivatives corresponding to the general formula

in which T represents a theophyllinyl-(7) or theobrominyl-(1) radical, ALk represents a linear or branched alkylene group with 2 to 5 carbon atoms, which may also be substituted by a hydroxy group, and Ar represents an aromatic monocyclic or condensed bicyclic carbocyclic or heterocyclic radical optionally substituted by one or more alkyl groups with 1 to 6 carbon atoms, alkenyl groups with 2 to 6 carbon atoms, alkinyl groups with 2 to 6 carbon atoms, hydroxy groups, acyloxy groups with 1 to 6 carbon atoms, alkoxy groups with 1 to 6 carbon atoms, alkenoxy groups with 2 to 6 carbon atoms, phenyl radicals, halogen atoms, amino groups, acyl groups with 2 to 6 carbon atoms (e.g., alkanoyl or benzoyl groups), aminocarbonyl groups, ureido groups, acyl amino groups with 1 to 6 carbon atoms (e.g., alkanoylamino or benzoylamino), cycloalkyl groups with 3 to 8 carbon atoms or by one or more cycloalkyenyl groups with 4 to 8 carbon atoms, the heterocyclic radical consisting of individual rings with 5 to 6 members and containing from 1 to 4 herteroatoms, preferably 1 to 2 heteroatoms, most preferably one heteroatom being nitrogen and if two heteroatoms are present the other being nitrogen or sulfur to their pharmaceutically acceptable salts and to processes for their production.

The compounds according to the invention show pharmacodynamic activity. In particular they block the β-receptors of the adrenergic nervous system. For example they have an inhibiting action on the circulatory effects induced by isoprenalin [1-(3,4-dihydroxyphenyl)-2-isopropyl amine ethanol]. Accordingly, the compounds according to the invention are particularly suitable for treating the following diseases: tacharrhythmia, angina pectoris, vegetative heart-function disorders, arterial hypertonia, phaochromocytoma, hyperkinetic heart syndrome.

The compounds according to the invention have a wide therapeutic scope and are distinguished by minimal side effects.

In the compounds of formula (I) according to the invention, the alkylene group Alk preferably consists of 2, 3 or 4 carbon atoms (ethylene groups, propylene groups, butylene group, the group —$CH_2$—$CH(OCH_)$—$CH_2$—, —$CH_2$—$(CH(OH))$—$(CH_2)_2$—, or —$(CH_2)_2$—$CH(OH)$—$CH_2$—). If the group Alk is branched, it contains particularly 3, 4 or 5 carbon atoms for example: —$CH_2$—$CH_2$—$CH(CH_3)$—, —$CH_2$—$CH(CH_3)$—, —$CH_2$—$CH(CH_3)$—$CH_2$—, —$CH_2$—$CH(CH_3)$—$CH(CH_3)$—, —$CH_2$—$CH(OH)$—$CH(CH_3)$—. If a hydroxy group is present, it is always in the alklyene moiety of Alk.

If the radical Ar is a carbocyclic radical, the carbocyclic radical in question is the phenyl or naphthyl radical (for example the naphthyl-(1)-radical, tetrahydronaphthyl, indanyl or indenyl radical. If Ar is a heterocyclic radical, the heterocyclic radical in question is, for example, a monocyclic 5-membered or 6-membered aromatic ring with one nitrogen, sulphur or oxygen atom or two nitrogen atoms or an aromatic condensed bicyclic radical or a phenyl ring with a 5-membered or 6-membered ring attached by condensation, the ring attached by condensation optionally containing a nitrogen, oxygen or sulphur atom. In the case of the bicyclic rings, the radical Ar is attached to the oxygen atom in particular through the 4-position or 5-position of the phenyl ring. Examples of the heterocyclic radical Ar, which may also be unsubstituted or substituted as described above, are indole, isoindole, benzimidazole, quinoline, dihydroquinoline, tetrahydroquinoline, isoquinoline, pyrazole, thiazole, methyl indole, methyl isoindole, methyl benzimidazole, methyl quinoline, methyl dihydroquinoline, methyl tetrahydroquinoline, methyl isoquinoline, methyl pyrazole, methyl thiazole, dimethyl indole, dimethyl quinoline, dimethyl isoquinoline, dimethylbenzimidazole thiazole (in the case of the bicyclic radicals, the methyl groups are preferably situated in the ring containing the heteroatom).

The substituents of the radical Ar have the following meaning in particular:

alkyl with 1 to 6 carbon atoms, for example methyl, ethyl, propyl, isopropyl, tert.-butyl, butyl, amyl or hexyl, with alkyl of 1 to 4 carbon atoms being preferred;

alkenyl with 2 to 5 carbon atoms, e.g., pentenyl, but preferably vinyl, allyl, methallyl, crotyl;

alkinyl with 2 to 5 carbon atoms, for example, ethinyl, propargyl;

cycloalkyl with a ring size of 3 to 8 carbon atoms, or more preferably 5 to 8 carbon atoms, most preferably cyclopentyl, cyclohexyl, cycloheptyl (although the cycloalkyl can also be cyclopropyl, cyclobutyl or cyclooctyl);

cycloalkenyl with a ring size of 5 to 8 carbon atoms, preferably cyclopentenyl, cyclohexenyl, cycloheptenyl (although the cycloalkenyl can also be cyclooctenyl);

alkoxy with 1 to 6 carbon atoms, for example, methoxy, ethoxy, propoxy, isopropyloxy, butoxy, tert.-butoxy, amyloxy or hexoxy with alkoxy of 1 to 4 carbon atoms being preferred;

alkenyloxy and alkinyloxy each with 2 to 5 carbon atoms, for example, vinyloxy, allyloxy, methallyloxy, crotyloxy, propargyloxy, with alkenyloxy of 3 to 4 carbon atoms being preferred;

halogen, preferably fluorine, bromine or chlorine;

acyl with 2 to 6 carbon atoms, for example, acetyl, propionyl, butyryl, pentanoyl, isobutyryl, hexanoyl, benzoyl;

acyl amino with 1 to 6, or more preferably, 1 to 5 carbon atoms, for example, acetamino, formyl amino, propionyl amino, butyryl amino, isobutyryl amino, pentanoyl amino, hexanoyl amino;

hydroxy or acyloxy with 2 to 6 carbon atoms, preferably with 2 to 4 carbon atoms such as acetoxy, propionyloxy, butyroxy, pentanoyloxy and hexanoyloxy;

amino carbonyl ($NH_2$—CO—) or ureido ($H_2N$—CO—NH—).

The substituents R may be the same or different. The radical Ar may contain several of the above-mentioned substituents, preferably 1, 2 or even 3 of these substitutents. Where Ar is a bicyclic heterocyclic ring, this ring preferably contains one of the above-mentioned substituents in the o-position to the heteroatom and/or an alkyl group on the nitrogen atom present, if any. A substitution of the phenyl group is particularly present in the o- and/or p-position.

In the context of the invention, the compounds of general formula (I) also include the possible stereoisomeric and optically active compounds and mixtures thereof, especially the racemates. Mixtures of diastereoisomers may be separated in known manner, for example, by fractional crystallisation. Optically active compounds may be obtained by the usual methods, for example, by recrystallising salts of the racemic bases of formula (I) with optically active acids or optionally by using optically active starting materials for the synthesis process.

The end products of formula (I) are obtained either in free form or in the form of their salts, depending upon the process conditions and starting materials used. The salts of the end product may be converted into the bases in known manner, for example, with alkali or ion exchangers. Salts can be obtained from the bases by reaction with organic or inorganic acids, especially those of the type which are suitable for forming therapeutically usable salts. The following are mentioned as examples of acids of this kind: hydrohalic acids, e.g., hydrochloric acid or hydrobromic acid, sulphuric acid, acids of phosphorus, e.g., phosphoric acid or phosphorus acid, nitric acid, perchloric acid, organic mono-, di- or tricarboxylic acids of the aliphatic, alicyclic, aromatic or heterocyclic series, also sulphonic acids. Examples of these organic acids are formic acid, acetic acid, propionic acid, succinic acid, glycolic acid, lactic acid, malic acid, tartaric acid, citric acid, ascorbic acid, maleic acid, fumaric acid, hydroxy maleic acid or pyruvic acid; phenyl acetic acid, benzoic acid, p-aminobenzoic acid, anthranilic acid, p-hydroxy benzoic acid, salicyclic acid or p-aminosalicyclic acid; embonic acid, methane sulphonic acid, ethane sulphonic acid, hydroxy ethane sulphonic acid, ethylene sulphonic acid, halogen benzene sulphonic acid, e.g., p-chlorobenzene sulphonic acid, toluene sulphonic acid, naphthalene sulphonic acid, suphanilic acid or even 8-chloroetheophylline.

In the processes described hereinafter for producing the compounds according to the invention, the amino groups which enter into reaction may contain the known and usual protective groups. Protective groups such as these as radicals which can readily be split off by hydrolysis or by hydrogenolysis and in many cases are actually split off during the reaction. In cases where protective groups of the kind in question are not split off during the process, they are split off after the reaction.

In many cases the starting materials already contain protective groups from their production.

These protective groups are for example acyl groups which can readily be split off by solvolysis or groups which can be split off by hydrogenation. The protective groups which can be split off by solvolysis are split off for example by saponification with dilute acids or by means of basic substances (potash, soda, aqueous alkali solutions, alcoholic alkali solutions, $NH_3$) at temperatures of from 10° to 150° C., more especially at temperatures of from 20° to 100° C. Groups which can be split off by hydrogenation, such as α-aryl alkyl radicals (benzyl radical) or hydroxy carbonyl radicals (carbobenzoxy radical), are best split off by catalytic hydrogenation in the present of the usual hydrogenation catalysts, especially palladium catalysts, platinum oxide or even Raney nickel, in a solvent or suspending agent, optionally under elevated pressure, at temperatures of from 20° to 100° C., more especially at temperatures of from 40° to 80° C. Examples of suitable solvents or suspensing agents are water, lower aliphatic alcohols, e.g., methanol, ethanol, isopropanol or butanol, cyclic ethers such as dioxane or tetrahydrofuran, aliphatic ethers, e.g., diethyl ether or dipropyl ether, dimethyl formamide and the like, also mixtures thereof.

The following are examples of protective groups which can be split off by hydrogenolysis: the benzyl radical, α-phenyl ethyl radical, benzyl radicals substituted in the benzene nuclues (e.g., p-bromo or p-nitro benzyl radical), carbobenzoxy radical, carbobenzthio radical, tert.-butyl hydroxy carbonyl radical. Examples of radicals which can be split off by hydrolysis are the trifluoroacetyl radical, phthalyl radical, trityl radical, p-toluene sulphonyl radical and the like, also lower alkenoyl radicals, such as the acetyl radical, formyl radical, propionyl radical, tert.-butyl carboxy radical and the like.

The protective groups normally used in the synthesis of peptides and the processes by which they are normally eliminated are particularly suitable. In this connection, references is made inter alia to the book by Jesse P. Greenstein and Milton Winitz entitled, *Chemistry of Amino Acids*, N.Y. 1961, John Wiley and Sons, Inc., Volume 2, for example pages 883 et seq. The carbolkoxy group (for example low molecular weight carbalkoxy group) is also suitable.

In cases where the starting materials also contain alcoholic hydroxy groups, and/or primary amino groups, these groups may also be protected by the above-mentioned protective groups which are subsequently eliminated in the same way.

The compounds according to the invention can be produced by:

(a) reacting a compound corresponding to the formula

T—Alk—Z      (II)

with a compound corresponding to the formula

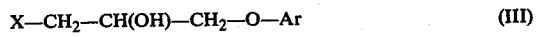

X—$CH_2$—CH(OH)—$CH_2$—O—Ar      (III)

in which T, Alk and Ar are as defined above whilst Z and X are different from one another and one represents an amino group or a protected amino group and the other represents a hydroxy group which is esterified by a strong organic or inorganic acid or which, in nonesterified form, may also form an ethylene oxide ring in conjunction with an adjacent, second hydroxy group, and splitting off any protective group present in the compounds thus obtained, or (b) in a compound corresponding to the general formula

T—Alk—NH—CH$_2$—CY—CH$_2$—O—Ar     (IV)

in which T, Alk and Ar are as defined above, Y represents oxygen or a hydroxy group plus hydrogen, the group Alk, instead of the hydroxy group, may also contain an oxo group and/or a double bond is present between the secondary nitrogen atom and the group Alk or the adjacent other CH$_2$-group, reducing one or two oxo groups and/or a double bond, or (c) reacting a compound corresponding to the general formula

AH     (V)

in which A is the theophyllinyl-(7) or theobrominyl-(1) radical or the radical ArO, or a metal salt thereof with a compound corresponding to the general formula

HO—B     (VI)

in which B is either the radical T—Alk—NH—CH$_2$—CH(OH)—CH$_2$ or the radical Alk—NH—CH$_2$—CH(OH)—CH$_2$—O—Ar, the secondary nitrogen atom of the radical B optionally containing one of the usual protective groups and the terminal hydroxy group of the formula HO—B either being esterified by a strong inorganic or organic acid or forming the ethylene oxide ring with an adjacent hydroxy group of the radical B, and splitting any protective group present, or (d) hydrolysing a compound corresponding to the formula

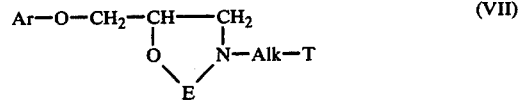

in which E is a carbonyl or alkylidene group, and optionally alkylating the compounds obtained, acylating an aromatic amino group or hydroxy group and/or converting the compounds obtained into their salts.

Method (a) may be carried out in the absence of an additional solvent or in a suitable solvent or dispersant. Examples of suitable solvents or dispersants are aromatic hydrocarbons such as, for example, benzene, toluene, xylene, mesitylene; ketones such as, for example, acetone, methyl ethyl ketone; halogenated hyrocarbons such as, for example, chloroform, carbon tetrachloride, chlorobenzene, methylene chloride; ethers such as, for example, tetrahydrofuran and dioxane; sulphoxides such as, for example, dimethyl sulphoxide; tertiary acid amides such as, for example, dimethyl formamide and N-methyl pyrrolidone; alcohols such as, for example, methanol, ethanol, isopropanol, amyl alcohol, tert.-butanol, etc. The reaction is carried out, for example, at temperatures in the range from 20° C. to 200° C. and preferably at temperatures in the range from 50° C. to 180° C. In cases where a solvent or dispersant is used, the reaction is frequently carried out at the reflux temperature thereof. In many cases, the reaction actually takes place at normal temperature, i.e., at a temperature of from 20° to 50° C.

It can be of advantage to use the starting compound of general formula (II) in excess and/or to add the reaction component of general formula (III) is dissolved or suspended form to the dissolved or suspended reaction component of general formula (II). The molar ratio between the compounds of general formulae (III) and (II) may amount to between 1:1 and 1:10 and optionally even higher.

For carrying out the reaction, it is possible, instead of using the ethylene oxide compound, also to use the corresponding halogen hydrin or a mixture of these two compounds (crude synthesis product) as the ethylene oxide starting compound.

The reaction may optionally be carried out in the presence of acid-binding agents, such as alkali metal carbonates, potash, soda, alkali hydroxides or tertiary bases.

In cases where Z or X is an esterified hydroxy group, the esters in question are reactive esters. A reactive ester is for example the ester of a strong organic or inorganic acid such as, above all, a hydrohalic acid, for example, hydrochloric acid, hydrobromic acid or hydriodic acid, or of a sulphonic acid, such as aryl or alkyl sulphonic acid, for example, p-toluene sulphonic acid. In cases where a reactive ester is used, the reaction is with advantage carried out especially in lower alcohols, e.g., methanol, ethanol or isopropanol, dioxane/water of dimethyl formamide/water in the presence of a basic condensation agent or an excess of amine.

In cases where Z or X is an amino group, this amino group may contain one of the above-mentioned protective groups, for example, a benzyl group. If these protective groups are not split off during the reaction itself, they may be removed in the manner described on completion of the reaction.

The starting materials of formula (III) are known or are produced by known processes, cf. for example the following literature references: German Offenlegungsschrift No. 2,323,354, for example pages 7 and 8; Pharmazie 30, No. 10 (1975), for example pages 635–636; Helvetica Chimica Acta, Vol. 54 (1971), pages 2414, 2418; Ber. deutsch. chem. Ges. 24 (1891), pages 2145 et seq.; J. Med. Chemistry 9 (1966) 155 et seq.; Methoden der organischen Chemie (Houben-Weyl) VI/3. page 424, 4th Edition 1965; cf. also J. Med Chemistry 11 (1968), pages 1009 et seq.

Compounds of formula (II) which contain an ethylene oxide ring are known or may be obtained in the same way as the known compounds (cf. for example Chemisches Zentralblatt 40 (1964), page 104).

Method (b) is carried out in a solvent or suspending agent at temperatures of, for example, from 20° to 150° C. and preferably at temperatures of from 40° to 150° C. The reaction is preferably carried out at an alkaline to neutral pH value. The reaction may even be carried out under elevated pressure (up to 50 atmospheres gauge). Examples of suitable solvents or suspending agents are lower aliphatic alcohols, for example those set forth above, alicyclic and cyclic ethers, for example those set forth above, dimethyl formamide, water and also mixtures thereof.

Suitable reducing agents are catalytically activated hydrogen using the usual metal catalysts (with and without supports), such as noble metal catalysts (palladium, palladium carbon, palladium on barium sulphate, PtO$_2$) or even Raney nickel. However, reduction may also be carried out with light metal hydrides, especially complex light metal hydrides (sodium borohydride, lithium aluminum hydride, lithium hydride, sodium triethoxy aluminum hydride and the like) or aluminum amalgam or aluminum alcoholates (for example aluminum isopropylate/isopropanol) and agents with a similar effect or, optionally, even with nascent hydrogen such as, for example, zinc/acid (zinc/glacial acetic acid, zinc/hydrochloric acid).

Any protective groups removable by hydrogenolysis are generally split off during reduction in cases where reduction is carried out with hydrogen in the presence of hydrogenation catalysts, especially palladium catalysts. If any protective groups present are not split off during the reaction, they are removed in the manner described on completion of the reaction.

The starting compounds of formula (IV) used in method (b) may be produced for example by condensing a compound corresponding to the formula

T—Alk′—V    (VIII)

with a compound corresponding to the formula

W—CHY—CH$_2$—O—Ar    (IX)

In formula (VIII), Alk′ represents a linear or branched alkylene group with 1 to 4 carbon atoms which, in cases where there are more than 2 carbon atoms, may also contain a hydroxy group or an oxo group and V represents either the group C(R)=O or the group —CHR—NH$_2$ where R is hydrogen or an alkyl group with 1 to 3 carbon atoms. In formula (IX), Y represents an oxygen atom or a hydroxy group plus hydrogen and W represents an aldehyde group or the group —CH$_2$NH$_2$. V and W are different from one another. The primary amino group in the groups —CHR—NH$_2$ and —CH$_2$—NH$_2$ is preferably protected by one of the above-mentioned protective groups, more especially a protective group which can be eliminated by hydrogenolysis, such as the benzyl group. The condensation of the compounds corresponding to formulae (VIII) and (IX) is generally carried out at temperatures in the range from 20° to 150° C., more especially at temperatures in the range from 40° to 100° C., in a solvent or dispersant, such as lower aliphatic alcohols, water-alcohol mixtures, dimethyl formamide or solvent mixtures containing dimethyl formamide. The Schiff's bases thus obtained are tautomeric with the corresponding oxazolidine form if adjacent hydroxy groups are present. For example, the Schiff's base of formula (X) is tautomeric with the oxazolidine form of formula (XI)

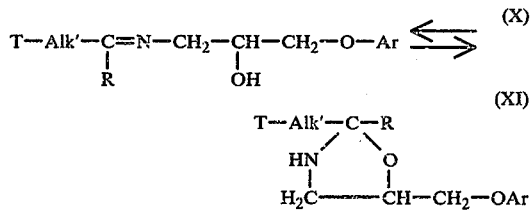

Accordingly, a state of equilibrium prevails between the two formulae. This is of no significance so far as reduction by method (b) is concerned. A corresponding tautomeric oxazolidine form may also be present if, in the compound of general formula (IV), the double bond is present between the secondary nitrogen atom and the adjacent CH$_2$—group and the group Alk contains a hydroxy group.

It is possible, instead of first isolating the reaction product obtained by reacting the compounds of formula (VIII) with compounds of formula (IX) for the reaction by method (b), immediately to treat it with the reducing agent in the same reaction medium. This applies in particular when catalytically activated hydrogen is used as the reducing agent. In this connection, it is equally possible for the reducing agent, especially catalytically activated hydrogen, to be present from the outset in the reaction of the compounds of formula (VIII) with compounds of formula (IX). Accordingly, a mixture of the starting components of formulae (VIII) and (IX) may also be used as starting compound of formula (IV) in method (b). This is possible in particular if Y is a hydroxy group plus hydrogen and/or the group Alk does not contain an oxo group.

In addition, starting compounds of formula (IV) may be obtained by reacting a compound of the formula T—Alk—Hal, in which T is as defined above, Alk is a linear or branched alkylene group with 2 to 5 carbon atoms, which is also substituted by a hydroxy group or an oxo group, and Hal is a halogen atom, under the conditions of method (a) with a compound NH$_2$—CH$_2$—CY—CH$_2$—O—Ar, in which Y and Ar are as defined above and the primary amino group may also be protected by one of the usual protective groups. A compound of the formula T—Alk—NH$_2$, in which T and Alk are as defined above and the amino group may also contain one of the usual protective groups may also be similarly reacted with a compound of the formula Hal—CH$_2$—CY—CH$_2$—O—Ar, in which Ar and Y are as defined above and Hal is a halogen atom, under the conditions of method (a).

Method (c) is normally carried out in a suitable solvent or dispersant in which the reactants are dissolved or suspended. Suitable solvents or dispersants are, for example, aromatic hydrocarbons such as, for example, benzene, toluene, xylene; ketones such as, for example, acetone, methyl ethyl ketone; halogenated hydrocarbons such as, for example, chloroform, carbon tetrachloride, chlorobenzene, methylene chloride; ethers such as, for example, tetrahydrofuran and dioxane; sulphoxides such as, for example, dimethyl sulphoxide; tertiary acid amides such as, for example, dimethyl formamide and N-methyl pyrrolidone. Polar solvents such as, for example, alcohols also represent particularly suitable solvents. Suitable alcohols are, for example, methanol, ethanol; isopropanol, tert.-butanol and the like. The reaction may be carried out for example in the presence of an acid-binding agent such as, for example, potash, soda, sodium bicarbonate. The reaction also be carried out in aqueous alkalis such as, for example, dilute sodium or potassium hydroxide. The reaction temperature may be in the range from 20° C. to the reflux temperature of the solvent or dispersant used. The reaction is generally carried out at temperatures in the range from 20° C. to 200° C. and preferably at temperatures in the range from 50° C. to 100° C.

Where the hydroxy group of the compound HO-B (formula VI) is present in ester form, the reaction is with advantage carried out in the presence of a basic condensation agent, more especially a compound capable of salt formation with the compound AH (alkali metal salt or alcoholate). Instead of this, it is also possible to use a preformed metal salt of the compound AH such as, for example, an alkali metal salt (K, Na) or even a silver salt or thallium salt.

The acid component of the esterified hydroxy group of the compound HO-B emanates from a strong organic or inorganic acid, more especially a hydrohalic acid, for example, hydrochloric acid, hydrobromic acid or hydriodic acid, or from a sulphonic acid such as an aryl or alkyl sulphonic acid, for example p-toluene sulphonic acid.

It can be of advantage to use the starting compound of general formula (VI) in an up to ten-fold molar excess and/or to add the reaction component of general formula (VI) in dissolved or suspended form to the dissolved or suspended reaction component of general formula (V). The molar ratio between the compounds of general formula (VI) and (VII) may amount to between 1:1 and 1:10 or even higher.

Starting compounds of general formula (VI), in which B is the group T—Alk—NH—CH$_2$—CH(OH)—CH$_2$, may be produced by reacting a compound T—Alk—NH$_2$ in the usual way with an epihalohydrin, preferably with epichlorohydrin or epibromohydrin.

The compound T—Alk—NH—CH$_2$—CH(OH)—CH$_2$—halogen or

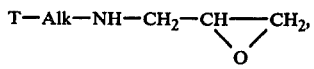

or a mixture of these two compounds, is obtained according to the reaction conditions. The reaction product thus formed may be isolated for further reaction, or alternatively may even be directly further reacted with the compound of formula (V) without isolation.

Starting compounds of formula (VI), in which B is the group —Alk—NH—CH$_2$—CH(OH)—CH$_2$—O—Ar and Alk is for example the group —CH$_2$—CH(OH)—CH$_2$—, one or both terminal CH$_2$'groups optionally being substituted by methyl or ethyl radicals, may be obtained in a manner similar to that just described by reacting a compound Ar—O—CH$_2$—CH(OH)—CH$_2$—NH$_2$ with a corresponding epihalogen hydrin. In addition, compounds of formula (VI), in which B represents the group —Alk—NH—CH$_2$—CH(OH)—CH$_2$—O—Ar or T—Alk—NH—CH$_2$—CH(OH)—CH$_2$— (meanings of Alk and Ar as defined in reference to formula I), may be obtained quite generally by reacting corresponding N-benzyl amines with epichlorohydrin or epibromohydrin or with an alkylene dihalide (Cl—Alk—Br), followed by debenzylation in accordance with Houben-Weyl, Methoden der Organischen Chemie 11/1 (4th Edition), pages 311-325, or Helevetica Chimica Acta 54 (1971), pages 2414 et seq. Accordingly, compounds of this kind are produced for example by reacting a compound T—Alk—NH(benzyl) or ArO—CH$_2$—CH(OH)—CH$_2$—NH(benzyl) in the usual way with epichloro(bromo)hydrin or even by reacting a compound ArO—CH$_2$—CH(OH)—CH$_2$—NH(Benzyl) in the usual way with Cl—Alk—Br. The benzyl group is then split off, for example by reduction, and the halogen hydrin converted with NaOH into the corresponding epoxide or the terminal halogen atom (chlorine atom) converted in known manner into the hydroxy group.

Method (d) is carried out in one of the usual solvents or suspending agents in the presence of an acid (sulphuric acid, hydrochloric acid and the like) or alkali (aqueous KOH, NaOH) at temperatures of for example from 0° to 150° C. The alkylidene group preferably contains from 1 to 6 carbon atoms ($>$CH$_2$, $>$CH—CH$_3$, $>$CH—C$_2$H$_5$, $>$C(CH$_3$)$_2$).

The starting compounds of formula (VII) may be obtained for example by reacting epoxides corresponding to the formula

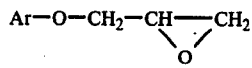

with N-alkyl urethanes of the formula T—Alk—N-H—COOR', in which R' is a lower alkyl group, in the presence or absence of solvents at temperatures of from 50° to 180° C. The urethanes just mentioned may be obtained for example from chloroformic acid alkyl esters and amino alkyl xanthines under the conditions described in Houben-Weyl, Methoden der Organischen Chemie, Volume 8, pages 138-139 (4th Edition).

In the starting compounds of general formula (VI), the secondary amino group and hydroxy groups present and also primary amino groups which substitute the radical Ar may contain protective groups. These protective groups may subsequently be removed in the manner described on completion of the reaction.

In the end products, any amino groups and/or hydroxy groups present in the radical Ar may be acylated with aliphatic acids containing 1 to 6 carbon atoms or with reactive acid derivatives thereof. Acylation may be carried out for example in inert solvents or suspending agents, such as dioxane, dimethyl formamide, benzene, toluene, at temperatures in the range from 0° to 200° C. Suitable acylating agents are ketenes and also acid chlorides or bromides, acid anhydrides or acid esters of aliphatic carboxylic acids with 1 to 6 carbon atoms, acylation optionally being carried out in the presence of an acid-binding agent such as potassium carbonate or sodium ethylate, or in the presence of a tertiary amine, for example triethyl amine. The esters are in particular esters with lower aliphatic alcohols. It is also possible initially to convert the groups (hydroxy group, amino group) to be acylated in the compound to be reached into the corresponding alkali metal compound by reacting them with an alkali metal, alkali metal hydride or alkali metal amide (especially sodium or sodium compounds) in an inert solvent, such as dioxane, dimethyl formamide, benzene or toluene, at temperatures of from 0° to 150° C. and subsequently adding the acylating agent.

In addition, end products in which the radical Ar contains hydroxy groups may be alkylated in the usual way on these hydroxy groups. Examples of suitable alkylating agents are esters of the formula RHal, ArSO$_2$OR and SO$_2$(OR)$_2$, where Hal is a halogen atom (especially chlorine, bromine or iodine) and Ar is an aromatic radical such as, for example, a phenyl or naphthyl radical optionally substituted by one or more lower alkyl radicals and R is a C$_1$-C$_6$ alkyl group or a C$_2$-C$_6$ alkenyl group. Examples are p-toluene sulphonic acid alkyl esters, e.g., methyl p-toluene sulphonate and ethyl p-toluene sulphonate, lower dialkyl sulphates, e.g., dimethyl sulphate and the like. The alkylating reaction is optionally carried out in the presence of the usual acid-binding agents, such as alkali metal carbonates, e.g., sodium carbonate or potassium carbonate, pyridine or other standard tertiary amines, at temperatures in the range from 0° to 150° C. in inert solvents such as alcohols, dioxane, dimethyl formamide, dimethyl sulphoxide, aromatic hydrocarbons such as benzene, toluene or acetone, also mixtures thereof.

Alkylation may even be carried out by way of corresponding metal salts (for example alkali metal salts). In addition, alkylation may also be carried out with diazoalkanes (1 to 6 carbon atoms) or diazoalkenes (2 to 6 carbon atoms).

Instead of using the above-mentioned alkylating and acylating agents, it is also possible to use other chemically equivalent agents of the kind commonly encountered in chemistry (cf. for example, L. F. and Mary Fieser, *Reagents for Organic Synthesis,* John Wiley and Sons, Inc., New York, 1967, Vol. 1, pages 1303-4, Vol. 2, page 471, Vol. 3, page 349, Vol. 4, page 581 and Vol. 5, page 767). Any acyl groups present in the compounds obtained may of course also be split off again in known manner.

In addition to the compounds set forth in the working examples other compounds within the invention include:

1-{3-[3-(1-naphthyloxy)-2-hydroxy propylamino]-propyl}-theobromine,
1-[3-(3-phenoxy-2-hydroxypropylamino)-propyl]-theobromine,
1-[3-(3-indolyl-(4)-oxy-2-hydroxypropylamino)]-propyl theobromine,
7-[2,3-dimethyl-2-(3-phenoxy-2-hydroxy-propylamino)propyl]-theophylline,
7-[3-(3-2',4'-dimethylphenoxy-2-hydroxy-propylamino)-propyl]-theophylline,
7-[3-(3-p-ethylphenoxy-2-hydroxypropylamino)-propyl]-theophylline,
7-[3-(3-o-butylphenoxy-2-hydroxypropylamino)-propyl]-theophylline,
7-[3-(3-p-hexylphenoxy-2-hydroxypropylamino)-propyl]-theophylline,
7-[2-(3-p-propargylphenoxy-2-hydroxy-propylamino)-propyl]-theophylline,
7-[3-(3-o-methyllylphenoxy-2-hydropropylamino)-propyl]-theophylline,
7-[3-(3-o-hydroxyphenoxy-2-hydroxypropylamino)-propyl]-theophylline,
7-[3-(3-2',4'-dihydroxyphenoxy-2-hydroxy-propylamino)-propyl]-theophylline,
7-[3-(3-2'-methyl-4'-hydroxyphenoxy-2-hydroxy-propylamino)-propyl]-theophylline,
7-[3-(3-p-acetylphenoxy-2-hydroxypropylamino)-propyl]-theophylline,
7-[3-(3-o-butyrylphenoxy-2-hydroxypropylamino)-propyl]-theophylline,
7-[3-(3-p-hexanoylphenoxy-2-hydroxypropylamino)-propyl]-theophylline,
7-[3-(3-p-benzoylphenoxy-2-hydroxypropylamino)-propyl]-theophylline,
7-[3-(3-p-butoxyphenoxy-2-hydroxypropylamino)-propyl]-theophylline,
7-[3-(3-o-hexoxyphenoxy-2-hydroxypropylamino)-propyl]-theophylline,
7-[3-(3-p-crotyloxyphenoxy-2-hydroxypropylamino)-propyl]-theophylline,
7-[3-(3-p-vinyloxyphenoxy-2-hydroxypropylamino)-propyl]-theophylline,
7-[3-(3-p-phenylphenoxy-2-hydroxypropylamino)-propyl]-theophylline),
7-[3-(3-2',4'-dichlorophenoxy-2-hydroxy-propylamino)-propyl]-theophylline,
7-[3-(3-2',4',5'-trichlorophenoxy-2-hydroxy-propylamino)-propyl]-theophylline,
7-[3-(3-p-bromophenoxy-2-hydroxypropylamino)-propyl]-theophylline,
7-[3-(3-o-fluorophenoxy-2-hydroxypropylamino)-propyl]-theophylline,
7-[3-(3-p-acetoxyphenoxy-2-hydroxypropylamino)-propyl]-theophylline,
7-[3-(3-o-butyryloxyphenoxy-2-hydroxypropylamino)-propyl]-theophylline,
7-[3-(3-p-hexanoyloxyphenoxy-2-hydroxypropylamino)-propyl]-theophylline,
7-[3-(3-p-aminophenoxy-2-hydroxypropylamino)-propyl]-theophylline,
7-[3-(3-o-aminocarbonylphenoxy-2-hydroxypropylamino)-propyl]-theophylline,
7-[3-(3-o-ureidophenoxy-2-hydroxypropylamino)-propyl]-theophylline,
7-[3-(3-p-formylaminophenoxy-2-hydroxypropylamino)-propyl]-theophylline,
7-[3-(3-p-butyrylaminophenoxy-2-hydroxypropylamino)-propyl]-theophylline,
7-[3-(3-o-hexanoxylaminophenoxy-2-hydroxypropylamino)-propyl]-theophylline,
7-[3-(3-o-propargyloxyphenoxy-2-hydroxypropylamino)-propyl]-theophylline,
7-[3-(3-o-cyclopentylphenoxy-2-hydroxypropylamino)-propyl]-theophylline,
7-[3-(3-p-cyclohexylphenoxy-2-hydroxypropylamino)-propyl]-theophylline,
7-[3-(3-o-cycloheptylphenoxy-2-hydroxypropylamino)-propyl]-theophylline,
7-[3-(3-p-cyclopentenylphenoxy-2-hydroxypropylamino)-propyl]-theophylline,
7-[3-(3-p-cyclohexenylphenoxy-2-hydroxypropylamino)-propyl]-theophylline,
7-[3-(3-quinolinyl-(2)-oxy-2-hydroxypropylamino)]-propyl theophylline,
7-[3-(3-pyrazolyl-(3)-oxy-2-hydroxypropylamino)]-propyl theophylline,
7-[3-(3-thiazolyl-(5)-oxy-2-hydroxypropylamino)]-propyl theophylline, and
7-[3-(3-benzimidazolyl-(2)-oxy-2-hydroxypropylamino)]-propyl theophylline.

The compounds of the invention are suited for the production of pharmaceutical compositions and preparations. The pharmaceutical compositions or drugs contain as the active material one or several of the compounds of the invention, in a given case in admixture with other pharmacologically or pharmaceutically effective materials. The production of the medicine can take place with the use of known and customary pharmaceutical assistants, carriers and diluents.

Such carriers and assistants as set forth for example are those recommended in the following literature as adjuvants for pharmacy, cosmetic and related fields such as in Ullmann's *Encyklopadie der technischer Chemie,* Vol. 4 (1953), pages 1 to 39; Journal of Pharmaceutical Sciences 52 (1963), pages 918 et seq.; H. v. Czetsch-Lindenwald, Hilftstoffe fur Pharmazie und angrenzende Gebiete; Pharm. Ind. 2 (1961), pages 72 et seq.; Dr. H. P. Fiedler, *Lexicon der Hilfstoffe fur Pharmazie, Kosmetik und angrenzende Gebiete,* Cantor Kg. Aulendorf i. Wurtt, 1971.

Examples of such materials include gelatin, natural sugars such as sucrose or lactose, lecithin, pectin, starch (for example corn starch), tylose, talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols (for example, methyl hydroxypropyl cellulose, methyl cellulose, hydroxyethyl cellulose), stearates, e.g., methylstearate and glyceryl stearate, magnesium and calcium salts of fatty acids with 12 to 22 carbon atoms, especially saturated acids (for example calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, mono-, di- and triglycerides of saturated fatty acids ($C_{12}H_{24}O_2$ to $C_{18}H_{36}O_2$ and their mixtures, e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400 and other polyethylene glycols, as well as derivatives of such alcohols and polyglycols, esters of saturated and unsaturated fatty acid (2 to 22 carbon atoms, especially 10 to 18 carbon atoms), with mono- (1 to 20 carbon atoms alkanols) or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, glycol furfural, tetrahydrofurfuryl alcohol, dimethyl acetamide, lactamide, lactates, e.g., ethyl lactate, ethyl carbonate, silicones (especially middle viscosity dimethyl polysiloxane), magnesium carbonate and the like.

For the production of solutions there can be used water or physiologically compatible organic solvents, as for example, ethanol, 1,2-propylene glycol, polyglycols, e.g., diethylene glycol, triethylene glycol and dipropylene glycol and their derivatives, dimethyl sulphoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g., monoacetic, diacetin, glyceryl monostearate, glyceryl distearate, glyceryl monopalmitate, paraffins and the like.

In the production of the preparations there can be used known and customary solution aids or emulsifiers. As solution aids and emulsifiers there can be used, for example, polyvinyl pyrrolidone, sorbitan fatty acid esters such as sorbitan trioleate, lecithin, gum acacia, gum tragacanth, polyoxyethylated sorbitan monooleate, polyoxyethylated fats, polyoxyethylated oleotriglycerides, linolized oleotriglycerides, polyethylene oxide-condensation products of fatty alcohols, alkylphenols or fatty acids. As used herein polyoxyethylated means that the materials in question contain polyoxyethylene chains whose degree of polymerization generally is between 2 and 40, particularly between 10 and 20.

Such polyoxyethylated materials for example can be obtained by reaction of hydroxyl group containing compounds (for example, mono- or diglycerides or unsaturated compounds such as, for example, those containing the oleic acid radical with ethylene oxide (for example, 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191–195).

Furthermore, there can be added preservatives, stabilizers, buffers, taste correctives, antioxidants and complex formers (for example, ethylene diamine tetracetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium meta bisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example, lower alkyl esters such as the methyl ester and the ethyl ester) benzoic acid, sodium benzoate, trichloroisobutyl alcohol, phenol, cresol, benzethonium chloride and formalin derivatives).

The pharmacological and galenical treatment of the compounds of the invention takes place according to the usual standard methods. For example, the active material or materials and assistants or carriers are well mixed by stirring or homogenization (for example, by means of a colloid mill or ball mill), wherein the operation is generally carried out at temperatures between 20° and 80° C., preferably 20° to 50° C.

The application of active material or drug can take place on the skin or mucous membrane or internally, for example, orally, enterally, rectally, lingually, intravenously, intramuscularly, intraperitoneally, intracutaneously or subcutaneously.

Particularly it is also possible or desirable to add other medicinally active materials, especially nitro compounds, e.g., nitroglycerine, heart glycosides, xanthine derivatives, coronary dilators, diuretics or blood pressure depressants. The compounds of the invention, for example, exhibit a good $\beta$-adrenolytic activity on the pattern of the tachycardia caused by Isoprenalin (isoproterenol) on waking rabbits. Waking cats, for example, after oral and intravenous addition, show a hypotonic effect.

For example, there is produced with the above-mentioned test methods at a dosage of 0.02 to 3 mg per kg of body weight (in rabbits) a 50% checking of the tachycardia.

This $\beta$-blocking activity is comparable to the activity of the known drug Propranolol.

The lowest effective dosage in the above-mentioned animal experiments was for example 0.02 mg/kg body weight, especially 0.02–0.05 mg/kg orally; 0.003 mg/kg intravenously.

As the general dosage range for the activity (based on animal tests such as above) there can be used for example 1–30 mg/kg orally, particularly 3–10 mg/kg; 0.001–1.0 mg/kg intravenously, particularly 0.02–0.5 mg/kg.

Besides the compounds of the invention have a stimulating effect. The negative inotropy and the increase of the breathing resistance are reduced thereby, which otherwise generally are coeffected by the $\beta$-blockage. Therefore, the compatibility is improved with the compounds of the invention and the danger of an overdosage is reduced. For example, the resorption and duration of effect are also improved. Furthermore, there is frequently caused an improvement of the peripheral blood flow and the cerebral blood flow.

In the therapy of the arterial hypertony there especially occurs a quicker appearance of activity with the compounds which lower the peripheral vessel resistance (improvement of the peripheral blood flow).

The pharmaceutical preparations generally contain between 1 and 300 mg of the active component or components of the invention.

The compounds can be delivered in the form of tablets, capsules, pills, dragees, plugs or in liquid form. As liquid forms there can be used for example oily or alcoholic or aqueous solutions as well as suspensions and emulsions. The preferred forms of use are tablets which contain between 1 and 200 mg of active material or solutions which contain between 0.1–10% of active material.

In individual doses the amount of active component of the invention can be used for example in an amount of:

a. in oral dispensation between 1 and 200 mg;
b. in parenteral dispensation (for example intravenously, intramuscularly) between 0.05 and 5 mg; and,
c. in rectal or vaginal dispensation between 10 and 500 mg.

(The dosages in each case are based on the free base.)

For example, there is recommended the use of 1 to 2 tablets containing 1 to 200 mg of active ingredient 3 times daily or for example, intravenously the injection 1 to 3 times daily of a 1 to 5 ml ampoule containing 0.1 to 5 mg of active substance. In oral preparations the minimum daily dosage should not be over 2 grams.

In veterinary medicine the compounds of the invention can be used for example prophylatically, e.g., in shipping pigs and other animals. There can be administered the above-mentioned dosages, e.g., 0.3–10 mg/kg body weight intravenously or 3–100 mg/kg body weight orally.

The acute toxicity of the compounds of the invention in the mouse (expressed by the $LD_{50}$ mg/kg method of Miller and Tainter, Proc. Soc. Exper. Biol. and Med. 57 (1944), pages 261 et seq.) in oral application is between 1000 mg/kg and 5000 mg/kg or above, e.g., 5000 mg/kg.

The drugs can be used in human medicine, in veterinary medicine, e.g., to treat cats, dogs, horses, sheep, cattle, goats and pigs or in agriculture. The drugs can be used alone or in admixture with other pharmacologically active materials.

The salts can also be used as curing agents for melamine-formaldehyde resins.

The invention is illustrated by the following Examples:

EXAMPLE 1

7-{3-[3-(1-naphthyloxy)-2-hydroxypropylamino]-propyl}-theophylline

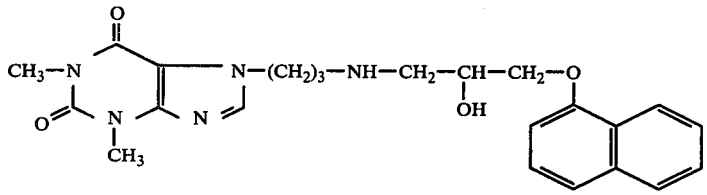

12.9 g of 1-chloro-3-(1-naphthyloxy)-2-propanol and 125 ml of xylene are added to 26 g of 7-(3-aminopropyl)-theophylline and the mixture obtained boiled under reflux with stirring for 67 hours. After cooling, the aminopropyl theophylline hydrochloride formed is filtered off under suction and the filtrate concentrated by evaporation in vacuo. The residue is dissolved in ethanol and the hydrochloride precipitated by the addition of alcoholic hydrochloric acid. 13 g of crude product are obtained, it can be purified by recrystallisation from methanol. Melting point of the hydrochloride: 209°–211° C.

EXAMPLE 2

7-[3-(3-phenoxy-2-hydroxypropylamino)-propyl]-theophylline

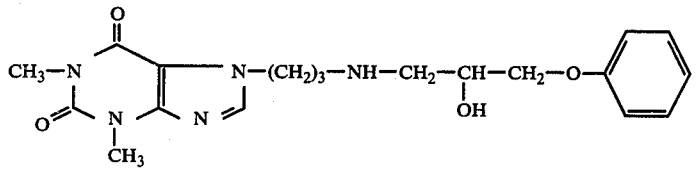

A mixture of 75 g of 7-(3-aminopropyl)-theophylline and 27.4 g of 1-chloro-3-phenoxy-2-propanol is heated for 8 hours at 130° to 140° C. After the melt has been cooled to 70°–90° C., ethanol is added to it, followed by brief boiling under reflux. After standing overnight, the untreated and precipitated aminopropyl theophylline hydrochloride is filtered off under suction, the filtrate is acidified with alcoholic hydrochloric acid, heavily concentrated and acetone added until crystallisation begins. The reaction product then separates and is recrystallised from methanol. Yield 30.2 g. Melting point of the hydrochloride: 183°–186° C.

The compounds identified in Table 1a below are obtained in the same way as described in the preceding Example. The corresponding quantities of the starting component of formulae II and III and also the respective reaction times and reaction temperatures are given in Table 1b below. In Table 1b, a few minor differences from the procedure of Example 2 are noted in the last column.

Table 1a

| Example No. | T—Alk—NH—CH₂—CH(OH)—CH₂—O—Ar | | | Melting point as hydro-chloride | Recrystallisation medium | Yield (g) |
|---|---|---|---|---|---|---|
| | T | Alk | Ar | | | |
| 3 /// radical | Theophyllinyl-(7) | —CH₂—CH₂— | naphthyl-(1)- | 242–244° C | ethanol/H₂O | 10.4 |
| 4 | Theophyllinyl-(7)- | —CH₂—CH₂—CH(CH₃)— |  | 232–235° C contains 1 mole of water of crystallisation | ethanol/H₂O | 27 |
| 5 | Theophyllinyl-(7)- | —CH₂—CH₂—CH(CH₃)— |  | 193–196° C | methanol (boiling with acetone) | 25.3 |
| 6 | Theophyllinyl-(7)- | —CH₂—CH₂— |  | 194–197° C | methanol (boiling with ethanol) | 43.2 |
| 7 | Theophyllinyl-(7)- | —CH₂—CH(CH₃)—CH₂— |  | 207–209° C | methanol (boiling with ethanol) | 20.5 |
| 8 | Theophyllinyl-(7)- | —(CH₂)₃— |  | 162–165° C | ethanol | 19.3 |
| 9 | Theophyllinyl-(7)- | —(CH₂)₃— |  | 172–175° C | ethanol | 24.4 |
| 10 | Theophyllinyl-(7)- | —(CH₂)₃— |  | 205–210° C | methanol (boiling with ethanol) | 26.3 |
| 11 | Theophyllinyl-(7)- | —CH₂—CH₂—CH(CH₃)— |  | 160–164° C | ethanol | 14 |
| 12 | Theophyllinyl-(7)- | —CH₂—CH₂—CH(CH₃)— |  | 188–196° C | ethanol-methanol | 15.5 |
| 13 | Theophyllinyl-(7)- | —CH₂—CH₂—CH(CH₃)— |  | 154–166° C | ethanol | 11.7 |
| 14 | Theophyllinyl-(7)- | —(CH₂)₃— |  | 156–160° C | methanol (boiling with acetone) | 17.8 |
| 15 | Theophyllinyl-(7)- | —CH₂—CH₂—CH(CH₃)— |  | 210–212° C | ethanol methanol | 15.4 |
| 16 | Theophyllinyl-(7)- | —(H₂)₃— |  | 157–162° C | acetone | 10.2 |
| 17 | Theophyllinyl-(7)- | —(CH₂)₃— |  | 145–147° C | ethanol (boiling with acetone) | 11.5 |
| 18 | Theophyllinyl-(7)- | —CH₂—CH₂—CH(CH₃)— |  | 248–250° C | aqueous methanol | 15.3 |
| 19 | Theophyllinyl-(7)- | —(CH₂)₃— |  | 216–219° C | methanol (boiling with ethanol) | 18.6 |
| 20 | Theophyllinyl-(7)- | —(CH₂)₄— |  | 173–176° C | ethanol (boiling with acetone) | 12 |
| 21 | Theophyllinyl-(7)- | —(CH₂)₃— |  | 226–228° C | methanol (boiling with acetone) | 22.9 |
| 22 | Theophyllinyl-(7)- | —CH₂CH₂—CH(CH₃)— |  | 248–250° C | methanol (boiling with ethanol) | 9.4 |
| 23 | Theophyllinyl-(7)- | —(CH₂)₄— |  | 168–170° C | methanol (boiling with acetone) | 28.7 |

Table 1a-continued

| Example No. | T—Alk—NH—CH$_2$—CH(OH)—CH$_2$—O—Ar | | | Melting point as hydro-chloride | Recrystallisation medium | Yield (g) |
|---|---|---|---|---|---|---|
| | T | Alk | Ar | | | |
| 24 | Theophyllinyl-(7)- | —(CH$_2$)$_3$— | O—CH$_2$—CH=CH$_2$ (phenyl) 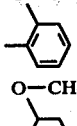 | 171–173° C | ethanol-methanol | 21.3 |
| 25 | Theophyllinyl-(7)- | —CH$_2$CH$_2$—CH(CH$_3$)— | O—CH$_2$—CH=CH$_2$ (phenyl)  | 147–149° C | ethanol (boiling with acetone) | 27.2 |

In the column headed "recrystallisation medium" in Table 1a, the words in brackets indicate that recrystallisation was followed by thorough boiling in the solvent named in the brackets.

Table 1b

| Example No. | Starting material of formula II | Starting material of formula III | Reaction time in hours/reaction temperature | Difference from product in accordance with Example 2 |
|---|---|---|---|---|
| 3 | 50 g of 7-(2-amino-ethyl)-theophylline | 26.6 g of 1-chloro-3-(1-naphthyoxy)-2-propanol | 8 / 140 – 150° C | The cooled reaction molt is dissolved in ethanol and the excess starting material II is precipitated by adding ether. The reaction product is obtained from the filtrate by adding alcoholic HCl. |
| 4 | 75 g of 7-(3-amino-butyl)-theophylline | 34.5 g of 1-chloro-3-(1-naphthyloxy)-2-propanol | 6 / 140 – 150° C | Nofiltration under suction and acidification of the filtrate. The reaction product recrystallised from aqueous ethanol is additionally boiled with acetone. |
| 5 | 69 g of 7-(3-amino-butyl)-theophylline | 25.7 g of 1-chloro-3-phenoxy-2-propanol | 8 / 130 – 140° C | none |
| 6 | 90.5 g of 7-(2-amino-ethyl)-theophylline | 38 g of 1-chloro-3-phenoxy-2-propanol | 6 / 140° C | none |
| 7 | 65.4 g of 7-(2-methyl-3-aminopropyl)-theophylline | 24.3 g of 1-chloro-3-phenoxy-2-propanol | 5 / 140° C | none |
| 8 | 50 g of 7-(3-amino-propyl)-theophylline | 21.1 g of 1-chloro-3-o-methylphenoxy-2-propanol | 8 / 140° C | none |
| 9 | 50 g of 7-(3-amino-propyl)-theophylline | 21.1 g of 1-chloro-3-m-methylphenoxy-2-propanol | 8 / 140° C | none |
| 10 | 50 g of 7-(3-amino-propyl)-theophylline | 21.1 g of 1-chloro-3-p-methylphenoxy-2-propanol | 8 / 130 – 140° C | none |
| 11 | 50 g of 7-(3-amino-butyl)-theophylline | 20 g of 1-chloro-3-o-methylphenoxy-2-propanol | 8 / 140° C | none |
| 12 | 50 g of 7-(3-amino-butyl)-theophylline | 20 g of 1-chloro-3-m-methylphenoxy-2-propanol | 8 / 140° C | none |
| 13 | 50 g of 7-(3-amino-butyl)-theophylline | 20 g of 1-chloro-3-p-methylphenoxy-2-propanol | 8 / 140° C | none |
| 14 | 50 g of 7-(3-amino-propyl)-theophylline | 23.4 g of 1-chloro-3-o-methoxyphenoxy-2-propanol | 8 / 130° C | none |
| 15 | 44 g of 7-(3-amino butyl)-theophylline | 19 g of 1-chloro-3-o-methoxyphenoxy-2-propanol | 8 / 130° C | none |
| 16 | 50.2 g of 7-(3-amino-butyl)-theophylline | 22.7 g of 1-chloro-3-o-allylphenoxy-2-propanol | 7 / 140° C | The reaction melt is heated under reflux with ethanol until a suspension is obtained. The procedure is then as in Example 2. By contrast, when the filtrate is worked up, it is not concentrated after acidification, instead absolute ether is added until clouding occurs and the reaction product is filtered off under suction on completion of crystallisation. |
| 17 | 47.5 g of 7-(3-amino-propyl)-theophylline | 22.7 g of 1-chloro-3-o-allylphenoxy-2-propanol | 7 / 140° C | as Example 16 |
| 18 | 50.2 g of 7-(3-amino-butyl)-theophylline | 22.1 g of 1-chloro-3-o-chlorophenoxy-2-propanol | 2 / 130 – 140° C | After acidification with alcoholic HCl, the filtrate is kept in a refrigerator for 24 hours, as a result of which the reaction product crystallises out. |
| 19 | 47.5 g of 7-(3-amino-propyl)-theophylline | 22.1 g of 1-chloero-3-o-chlorophenoxy-2-propanol | 2 / 130 – 140° C | as Example 18 |
| 20 | 47.5 g of 7-(4-amino-butyl)-theophylline | 22.1 g of 1-chloro-3-o-chlorophenoxy-2- | 2 / 120 – 125° C | as Example 18 |

Table 1b-continued

| Example No. | Starting material of formula II | Starting material of formula III | Reaction time in hours/reaction temperature | Difference from product in accordance with Example 2 |
|---|---|---|---|---|
| 21 | 47.5 g of 7-(3-amino-propyl)-theophylline | 24.4 g of 4-(3-chloro-2-hydroxypropoxy)-acetanilide | 2.5 / 110 – 120° C | After acidification the filtrate is not concentrated, but instead ether is added until clouding occurs and the reaction product is filtered off under suction on completion of crystall-isation. The reaction product recrystallised from methanol is again boiled with ethanol. |
| 22 | 50.2 g of 7-(3-amino-butyl)-theophylline | 24.4 g of 4-(3-chloro-2-hydroxypropoxy)-acet-anilide | 2.5 / 110 – 120° C | as Example 21 |
| 23 | 50.2 g of 7-(4-amino-butyl)-theophylline | 24.4 g of 4-(3-chloro-2-hydroxypropoxy)-acet-anilide | 2.5 / 110 – 120° C | as Example 21 |
| 24 | 47.5 g of 7-(3-amino-propyl)-theophylline | 24.2 g of 1-chloro-3-o-allyloxyphenoxy-2-propanol | 2.5 / 110 – 120° C | as Example 21 |
| 25 | 50.2 g of 7-(3-amino-butyl)-theophylline | 24.2 g of 1-chloro-3-o-allyloxphenoxy-2-propanol | 2.5 / 110 – 120° C | as Example 21 |

EXAMPLE 26

7-[3-(3-indolyl-(4)-oxy-2-hydroxypropylamino)]-propyl theophylline

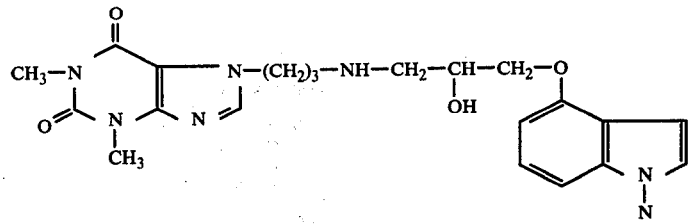

4-(2,3-epoxypropoxy)-indole, which has been produced in the manner described below from 14.5 g of 4-hydroxy indole and 10.6 g of epichlorohydrin and which still contains a small quantity of 1-chloro-3-indo-lyl-(4)-oxy-2-propanol, is stirred for 3 hours at 125° C. together with 30 g of 7-(3-aminopropyl)-theophylline. 20 ml of water and 100 ml of chloroform are added to the cooled, but still warm reaction product. After stirring for a few minutes, the chloroform phase is separated off in a separation funnel and extracted twice by shaking with 50 ml of water. The chloroform solution dried with sodium sulphate is distilled off in vacuo to dryness, the residue is dissolved in 70 ml of ethanol and weakly acidified with alcoholic hydrochloric acid. Filtration under suction and drying in a vacuum drying cabinet leaves 23 g of hydrochloride which is purified by recrystallisation from 90% ethanol. Melting point of the hydrochloride: 248°–250° C.

The base is precipitated from the aqueous solution of the hydrochloride with 1N NaOH and recrystallised from ethanol (Mp: 138° C.).

If a mixture of 2.0 g of this base and 1.0 g of 8-chloro-theophylline is dissolved in hot ethanol and the resulting solution left standing overnight in a refrigerator, 2.5 g of crystalline 8-chlorotheophylline salt of the above compound are obtained. Melting point: 203° C.

Production of the starting material 4-(2,3-epoxy-propoxy)-indole: 14.5 g of 4-hydroxy indole are added with vigorous stirring to a solution of 4.5 g of sodium hydroxide in 100 ml of water while nitrogen is introduced. After 15 minutes, 10.6 g of epichlorohydrin are added, followed by stirring for 20 hours at 25° C. After extraction by shaking with methylene chloride, the methylene chloride extract is dried with sodium sulphate and the solvent distilled off in vacuo. The residual oil is directly further reacted.

The compounds identified in Table 2a below are obtained in the same way as described in the preceding Example. The corresponding quantities of the starting components of formulae II and III, the respective reaction times and reaction temperatures and also minor differences are shown in Table 2b below.

Table 2a

| Ex. No. | T | T—Alk—NH—CH$_2$—CH(OH)—CH$_2$—O—Ar | | Melting point of the base | Recrystall-isation medium | Yield (g) |
|---|---|---|---|---|---|---|
| | | Alk | Ar | | | |
| 27 | theophyllinyl-(7)- | —CH$_2$—CH$_2$—CH(CH$_3$)— | indolyl-(4)-oxy radical | 68–70° C(8-chlorotheo-phyllinate: 215° C) | isopropanol | 2.5 |
| 28 | theophyllinyl-(7)- | —CH$_2$—CH$_2$—CH(CH$_3$)— | 2-methyl-indolyl-(4)-oxy radical | 146° C | isopropanol | 3.4 |
| 29 | theophyllinyl-(7)'- | —(CH$_2$)$_3$— | 2-methyl indolyl-(4)-oxy radical | 168–172° C | isopropanol | 3.7 |
| 30 | theophyllinyl-(7)- | —CH$_2$—CH$_2$— | 2-methyl indolyl- | 114–116° C | isopropanol | 2.1 |

Table 2a-continued

| Ex. No. | T | T—Alk—NH—CH₂—CH(OH)—CH₂—O—Ar Alk | Ar | Melting point of the base | Recrystall- isation medium | Yield (g) |
|---|---|---|---|---|---|---|
| 31 | theophyllinyl-(7)- | —CH₂—CH(OH)—CH₂— | (4)-oxy radical 2-methyl indolyl- | 175–178° C | ethanol | 1.8 |
| 32 | theophyllinyl-(7)- | —(CH₂)₃— | (4)-oxy radical 2,3-dimethyl indolyl (4)-oxy radical | HCl salt : 285–288° C (decomposition) | HCl salt: 70% ethanol then 80% methanol | 3 |
| 33 | theophyllinyl-(7)- | —CH₂—CH₂—CH(CH₃)— | 2,3-dimethyl indolyl-. HCl salt: (4)-oxy radical | HCl salt: 262–264° C (decomposition) | 80% isopropanol | 2.7 |

Table 2b

| Ex. No. | Compound of formula II | Starting compound of formula III | Reaction time in hours/ reaction temperature and any differences from Example 26 |
|---|---|---|---|
| 27 | 15.2 g of 7-(3-aminobutyl)- theophylline | 4-(2,3-epoxypropoxy)-indole, crude product of 8.3 g of 4-hydroxy indole and 6.1 g of epichloohydrin | 3 / 125° C |
| 28 | 15.7 g of 7-(3-aminobutyl)- theophylline | 2-methyl-4-(2,3-epoxypropoxy)-indole, crude product of 9.5 g of 2-methyl-4-hydroxy indole and 6.2 g of epichlorohydrin | 3 / 125° C |
| 29 | 19g of 7-(3-aminopropyl)- theophylline | 2-methyl-4-(2,3-epoxypropoxy)-indole, crude product of 5.9 g of 2-methyl-4-hydroxy indole 3.85 g of epichlorohydrin | 3 / 125° C |
| 31 | 19.5 g of 7-(2-hydroxy- 3-aminopropyl)-theophylline | 2-methyl-4-(2,3-epoxypropoxy)-indole, crude product of 5.9 g of 2-methyl-4-hydroxy indole and 3.85 g of epichlorohydrin | 3 / 125° C |
| 32 | 16.3 g of 7-(3-amino- propyl)-theophylline | 2,3-dimethyl-4-(2,3-epoxypropoxy)- indole, crude product of 5.7 g of 2,3-dimethyl-4-hydroxy indole and 3.3 g of epichlorohydrin | 3/110–120° C (under nitrogen). The chloroform residue is dissolved in 200 ml of ethanol. |
| 33 | 17.3 g of 7-(3-aminobutyl) -theophylline | 2,3-dimethyl-4-(2,3-epoxypropyl)- indole, crude product of 5.7 g of 2,3-dimethyl-4-hydroxy indole and 3.3 g of epichlorohydrin | 5/102° C in the presence of 50 ml of dioxane. After heating, the product is concentrated by evaporation in vacuo and the residue taken up in chloroform and further processed in the manner described. |

EXAMPLE 34

7-[3-(3,2'-methyl indolyl-(4)-oxy-2-hydroxypropylamino)-propyl]-theophylline

This is the same compound which was produced in Example 29. Now, however, the amino group of the starting component II contains a protective group removable by hydrogenolysis.

24.8 g of 7-(3-benzylaminopropyl)-theophylline are heated with stirring for 3 hours to 130° C. with crude 2-methyl-4-(2,3-epoxypropoxy)-indole obtained from 5.9 g of 2-methyl-4-hydroxy indole. Following the addition of chloroform and water, stirring is continued, the layers are separated, the chloroform phase is extracted by shaking twice with water, the chloroform extract is dried with sodium sulphate and the solvent is distilled off. The hydrochloride is precipitated from the alcoholic solution of the residue by acidification with alcoholic hydrochloric acid. The salt recrystallised from ethanol is hydrogenated in alcoholic solution at 60° C./6 atmospheres in the presence of 0.5 g of 5% palladium-carbon catalyst. The filtered reaction solution is concentrated by evaporation in vacuo, the residue is taken up in water and the base described in Example 29 is precipitated with 1N NaOH. Yield: 1.8 g; Melting point: 168°–170° C.

EXAMPLE 35

7-[2-(3-naphthyl-(1)-oxy-2-hydroxypropylamino)- propyl]-theophylline

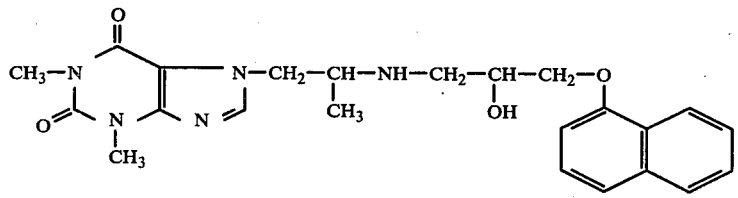

(Method b)

23.4 g of 1-benzylamino-3-(1-naphthyloxy)-2-propanol and 15.0 g of 7-acetonyl theophylline, or the condensation product obtained therefrom, are hydrogenated in 300 ml of ethanol at 60° C. in the presence of 3 g of 5% palladium carbon. After the hydrogen has been absorbed, the mixture is filtered, the solvent is distilled off and the solution of the residue in methanol acidified with isopropanolic hydrochloric acid. Acetone is added until permanent clouding occurs, after which the mixture is left standing for 2 days at room temperature. The hydrochloride precipitated is filtered off under suction, recrystallised from methanol and boiled in acetone. Yield: 7.5 g; melting point of the hydrochloride: 203°–206° C.

Examples of pharmaceutical formulations of the compound of Example 28 are given below:

Injection Solution 1 mg of the compound of Example 28 in the form of the hydrochloride salt was dissolved in 200 mg of propylene glycol and the solution filled up with water to a total volume of 2 ml. After filtration, the solution is filled into ampoules.

Tablets:
A 150 mg tablet contained:

| Compound of Example 28 | 50.0 mg |
| Lactose | 79.1 mg |
| Polyvinylpyrrolidone | 5.0 mg |
| Cornstarch | 15.0 mg |
| Highly dispersed silica | 0.5 mg |
| Magnesium stearate | 0.4 mg |

The compound of Example 28 was mixed with lactose and cornstarch and moistened with a solution of polyvinyl pyrrolidone in water; the composition was thoroughly worked, dried, sieved and after addition of the highly dispersed silica and magnesium stearate pressed into tablets.

The compositions can comprise, consist essentially of or consist of the materials set forth.

What is claimed is:

1. A compound of the formula

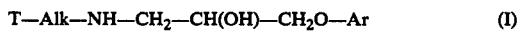

$$T-Alk-NH-CH_2-CH(OH)-CH_2O-Ar \qquad (I)$$

in which T represents theophyllinyl-(7) or theobrominyl-(1), Alk is alkylene group with 2 to 5 carbon atoms or alkylene group with 2 to 5 carbon atoms substituted by hydroxy group and Ar represents an unsubstituted aromatic benzene or naphthalene or heterocyclic ring or such aromatic ring substituted by alkyl with 1 to 6 carbon atoms, alkenyl with 2 to 6 carbon atoms, alkinyl with 2 to 6 carbon atoms, hydroxy, alkanoyloxy with 2 to 6 carbon atoms, alkoxy with 1 to 6 carbon atoms, alkenoxy with 2 to 6 carbon atoms, phenyl, halogen, amino, alkanoyl with 2 to 6 carbon atoms, aminocarbonyl, ureido, alkanoylamino with 1 to 6 carbon atoms, cycloalkyl with 3 to 8 carbon atoms or a cycloalkenyl with 4 to 8 carbon atoms, the heterocyclic ring being indole ring or insoindole ring, or pharmaceutically acceptable salt thereof.

2. A compound according to claim 1 wherein the substituent on the aromatic ring is alkyl of 1 to 4 carbon atoms, alkenyl of 2 to 4 carbon atoms, alkinyl of 3 carbon atoms, cycloalkyl with 5 to 7 carbon atoms, cycloalkenyl with 5 to 7 carbon atoms, hydroxy, alkanoyloxy with 2 to 6 carbon atoms, alkoxy with 1 to 4 carbon atoms, alkenoxy with 3 to 4 carbon atoms, phenyl, halogen of atomic weight 9 to 80, amino, alkanoyl with 2 to 6 carbon atoms, aminocarbonyl, ureido, alkanoylamino with 1 to 5 carbon atoms.

3. A compound according to claim 2 wherein T is theophyllinyl-(7) radical.

4. A compound according to claim 3 wherein the aromatic ring of Ar is benzene, naphthalene or indole.

5. A compound to claim 4 wherein Ar is α-naphthyl, phenyl, methylphenyl, methoxyphenyl, allylphenyl, chlorophenyl, acetylaminophenyl, allyloxyphenyl, indolyl, methyl indolyl or dimethyl indolyl.

6. A compound according to claim 5 wherein Alk is alkyl of 2 to 4 carbon atoms of 2-hydroxypropylene.

7. A compound according to claim 3 wherein Alk is trimethylene or branched alkylene group of 3 to 5 carbon atoms.

8. A compound according to claim 7 wherein Ar is α-naphthyl, phenyl, o-allyloxyphenyl, p-allyloxyphenyl, indolyl-(4), 2-methylindolyl-(4) or 2,3-dimethylindolyl-(4).

9. A medicament containing as an active ingredient a compound of claim 1 together with a pharmacological excipient or diluent.

10. A method of blocking β-receptors of the adrenergic nervous system of a mammal comprising administering to the mammal an effective amount to block said β-receptor of a compound of claim 1.

11. A method according to claim 10 wherein there is administered at least 0.2 mg/kg body weight of the mammal.

12. A compound according to claim 1 wherein Ar is the heterocyclic ring and is indole ring or isoindole ring.

13. A compound according to claim 12 wherein the heterocyclic ring is indole ring.

14. A compound according to claim 13 wherein Ar is unsubstituted indolyl or indolyl substituted with alkyl of 1 to 4 carbon atoms.

15. A compound according to claim 14 wherein Ar is indolyl, methyl indolyl or dimethyl indolyl.

16. A compound according to claim 15 wherein T is theophyllinyl-(7).

17. A compound according to claim 15 wherein Ar is indolyl-(4), 2-methylindolyl-(4) or 2,3-dimethylindolyl-(4).

18. A compound according to claim 16 wherein Alk is alkyl of 2 to 4 carbon atoms or 2-hydroxypropylene.

19. A compound according to claim 16 wherein Alk is trimethylene or branched alkylene group of 3 to 5 carbon atoms.

20. A compound according to claim 16 wherein Alk is —CH$_2$CH$_2$CH(CH$_3$)— and Ar-O is 2-methylindolyl-(4)-oxy.

21. A compound according to claim 16 wherein Alk is —CH$_2$CH$_2$CH(CH$_3$)— and Ar-O is indolyl-(4)-oxy.

22. A compound according to claim 16 wherein Alk is —(CH$_2$)$_3$— and Ar-O is 2-methylindolyl-(4)-oxy.

23. A compound according to claim 16 wherein Alk is —CH$_2$CH$_2$CH(CH$_3$)— and Ar-O is 2,3-dimethylindolyl-(4)-oxy.

24. A medicament having as an active ingredient a compound of claim 14 together with a pharmacological excipient or diluent.

25. A method of blocking β-receptors of the adrenergic nervous system of a mammal comprising the step of administering to the mammal an effective amount to block said β-receptor of a compound of claim 14.

26. A method according to claim 25 wherein there is administered at least 0.2 mg/kg body weight of the mammal.

27. A medicament in unit dosage form having between 1 and 300 mg of a compound of claim 1 together with a pharmacological excipient or diluent.

* * * * *

UNITED STATES PATENT AND TRADEMARK OFFICE
CERTIFICATE OF CORRECTION

PATENT NO. : 4,144,340

DATED : March 13, 1979

INVENTOR(S) : Offermanns, Heribert; Klingler, Karl; Thiemer, Klaus and Stroman, Fritz It is certified that error appears in the above-identified patent and that said Letters Patent are hereby corrected as shown below:

Cover sheet, item 30 "1554/76" should be "15547/76".

Signed and Sealed this

*Eighteenth* Day of *September 1979*

[SEAL]

*Attest:*

*Attesting Officer*

LUTRELLE F. PARKER

*Acting Commissioner of Patents and Trademarks*